(12) United States Patent
Knoll (10) Patent No.: US 8,727,963 B2
(45) Date of Patent: May 20, 2014

(54) METHODS AND IMPLANTS FOR TREATING URINARY INCONTINENCE

(75) Inventor: L. Dean Knoll, Brentwood, TN (US)

(73) Assignee: AMS Research Corporation, Minnetonka, MN (US)

( * ) Notice: Subject to any disclaimer, the term of this patent is extended or adjusted under 35 U.S.C. 154(b) by 621 days.

(21) Appl. No.: 12/533,515

(22) Filed: Jul. 31, 2009

(65) Prior Publication Data

US 2010/0030016 A1 Feb. 4, 2010

Related U.S. Application Data

(60) Provisional application No. 61/085,247, filed on Jul. 31, 2008.

(51) Int. Cl.
*A61F 2/02* (2006.01)

(52) U.S. Cl.
USPC ............. 600/30; 600/37; 606/144; 66/63; 604/264

(58) Field of Classification Search
USPC ............ 600/30, 37; 606/144; 66/63; 604/264
See application file for complete search history.

(56) References Cited

U.S. PATENT DOCUMENTS

| | | |
|---|---|---|
| 2,738,790 A | 3/1956 | Todt et al. |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS

"We're staying ahead of the curve" Introducing the IVS Tunneller Device for Tension Free Procedures, Tyco Healthcare, 3 pages (2002).

(Continued)

*Primary Examiner* — Christine Matthews
*Assistant Examiner* — Sunita Reddy
(74) *Attorney, Agent, or Firm* — Kagan Binder, PLLC (57) ABSTRACT

Described are methods, implants, insertion tools, and related systems and kits, for placing an implant to treat urinary incontinence; the implants include soft tissue anchors that are capable of engaging needles of the insertion tools, and the implants are designed to place a central support portion at a location to support a urethra with extension portions and soft tissue anchors extending to tissue at regions of an obturator foramen.

15 Claims, 3 Drawing Sheets

(56) References Cited

U.S. PATENT DOCUMENTS

| | | |
|---|---|---|
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Rizvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |

(56) References Cited

U.S. PATENT DOCUMENTS

| | | |
|---|---|---|
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,198,597 B2 | 4/2007 | Siegel et al. |
| 7,226,407 B2 | 6/2007 | Kammerer et al. |
| 7,226,408 B2 | 6/2007 | Harai et al. |
| 7,229,404 B2 | 6/2007 | Bouffier |
| 7,229,453 B2 | 6/2007 | Anderson et al. |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosley et al. |
| 7,789,821 B2 | 9/2010 | Browning |
| 2001/0049467 A1 | 12/2001 | Lehe et al. |
| 2002/0007222 A1 | 1/2002 | Desai |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0133217 A1* | 7/2004 | Watschke ................. 606/148 |
| 2004/0225181 A1 | 11/2004 | Chu et al. |
| 2004/0230206 A1* | 11/2004 | Gellman et al. ............. 606/148 |
| 2004/0267088 A1 | 12/2004 | Kammerer |
| 2005/0000523 A1 | 1/2005 | Beraud |
| 2005/0004427 A1 | 1/2005 | Cervigni |
| 2005/0038451 A1 | 2/2005 | Rao et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0028828 A1 | 2/2006 | Cox et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | Landgrebe |
| 2007/0173864 A1 | 7/2007 | Chu |
| 2008/0027271 A1* | 1/2008 | Maccarone ................. 600/30 |
| 2008/0039678 A1 | 2/2008 | Montpetit et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0221868 A1 | 9/2009 | Evans |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9317635 A1 | 9/1993 |

(56) References Cited

FOREIGN PATENT DOCUMENTS

| | | |
|---|---|---|
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0074594 A1 | 12/2000 |
| WO | WO0074613 A1 | 12/2000 |
| WO | WO0074633 A2 | 12/2000 |
| WO | WO0106951 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004034912 A1 | 4/2004 |
| WO | WO2005037132 A2 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Araki, Tohru et al., The Loop-Loosening Procedure for Urination Difficulties After Stamey Suspension of the Vesical Neck, The Journal of Urology, vol. 144, pp. 319-323 (Aug. 1990).

Asmussen. M., etal., Simultaneous Urethro-Cystometry With a New Technique:, Scand J Urol Nephrol 10, p. 7-11 (1976).

Beck, Peter R. et al., Treatment of Urinary Stress Incontinence With Anterior Colporrhaphy, Obstetrics and Gynecolooy, vol. 59 (No. 3) pp. 269-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).

Blaivas, Jerry et al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blaivas, Jerry, Commentary: Pubovaginal Sling Procedure, Experience with Pubovaginal Slings, pp. 93-101 (1990).

Boyles, Sarah Hamilton et al., Procedures for Urinary Incontinence in the United States, 1979-1997, Am J Obstet Gynecol, vol. 169, No. 1, pp. 70-75 (Jul. 2003).

Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Capio™ CL—Transvaginal Suture Capturing Device—Transvaginal Suture Fixation to Cooper's Ligament for Sling Procedures, Boston Scientific, Microvasive®, 8 pages, (2002).

Cervigni, Mauro et al., The Use of Synthetics in the Treatment of Pelvic Organ Prolapse, Voiding Dysfunction and Female Urology, vol. 11, pp. 429-435 (2001).

Choe, Jong M. et al., Gore-Tex Patch Sling: 7 Years Later, Urology, vol. 54, pp. 641-646 (1999).

Cook/Ob Gyn®, Urogynecology, Copyright Cook Urological Inc., pp. 1-36 (1996).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Das, Sakti et al., Laparoscopic Colpo-Suspension, The Journal of Urology, vol. 154, pp. 1119-1121 (Sep. 1995).

Debodinance, Philipp et al., "Tolerance of Synthetic Tissues in Touch With Vaginal Scars: Review to the Point of 287 Cases", Europeon Journal of Obstetrics & Gynecology and Reproductive Biology 87 (1999) pp. 23-30.

Decter, Ross M., Use of the Fascial Sling for Neurogenic Incontinence: Lessons Learned, The Journal of Urology, vol. 150, pp. 683-686 (Aug. 1993).

(56) References Cited

OTHER PUBLICATIONS

Delancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).

Delorme, Emmanuel, Trans-Obturator Sling: A Minimal Invasive Procedure to Treat Female Stress Urinary Incontinence. Progres en Urologie, vol. 11, pp. 1306-1313 (2001) English Abstract attached.

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69, pp. 45-50 (1990).

Falconer, C. et al., Clinical Outcome and Changes in Connective Tissue Metabolism After Intravaginal Slingplasty in Stress Incontinence Women, International Urogynecology Journal, pp. 133-137 (1966).

Falconer, C. et al., Influence of Different Sling Materials of Connective Tissue Metabolism in Stress Urinary Incontinent Women, International Urogynecology Journal, Supp. 2, pp. S19-S23 (2001).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).

Flood, C.G. et al., Anterior Colporrhaphy Reinforce with Marlex Mesh for the Treatment of Cystoceles, International Urogynecology Journal, vol. 9, pp. 200-204 (1998).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology, vol. 138 (Sep. 1987).

Guner, et al., Transvaginal Sacrospinous Colpexy for Marked Uterovaginal and Vault Prolapse, Inter J of Gynec & Obstetrics, vol. 74. pp. 165-170 (2001).

Gynecare TVT Tension-Free Support for Incontinence, The tension-free solution to female Incontinence, Gynecare Worldwide,6 pages, (2002).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Heit, Michael et al., Predicting Treatment Choice for Patients With Pelvic Organ Prolapse, Obstetrics and Gynecology, vol. 101, n. 6, pp. 1279-1284 (Jun. 2003).

Henriksson, L., et al. A Urodynamic Evaluation of the Effects of Abdominal Urethrocystopexy and Vaginal Sling Urethroplasty in Women with Stress Incontinence, Am. J. Obstet. Gynecol. vol. 131, No. 1, pp. 77-82 (Mar. 1, 1978).

Hodgkinson, C. Paul et.al., Urinary Stress Incontinence in the Female, Department of Gynecology and Obstetrics, Henry Ford Hospital, vol. 10, No. 5, pp. 493-499, (Nov. 1957).

Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).

Ingelman-Sunberg, A. et al., Surgical Treatment of Fmeal Urinary Stress Incontinence, Contr. Gynec. Obstet., vol. 10, pp. 51-69 (1983).

IVS Tunneller—A Universal instrument for anterior and posterior intra-vaginal tape placement, Tyco Healthcare, 4 pages (Aug. 2002).

IVS Tunneller—ein universelles Instrument fur die Intra Vaginal Schlingenplastik, Tyco Healthcare, 4 pages (2001).

Jeffcoate, T.N.A. et al., The Results of the Aldridge Sling Operation for Stress Incontinence, Journal of Obstetrics and Gynaecology, pp. 36-39 (1956).

Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).

Julian, Thomas, The Efficacy of Marlex Mesh in the Repair of Sever, Recurrent Vaginal Prolapse of the Anterior Midvaginal Wall, Am J Obstet Gynecol, vol. 175, No. 6, pp. 1472-1475 (Dec. 1996).

Karram, Mickey et al., Patch Procedure: Modified Transvaginal Fascia Lata Sling for Recurrent for Severe Stress Urinary Incontinence, vol. 75, pp. 461-463 (Mar. 1990).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Kersey, J., The Gauze Hammock Sling Operation in the Treatment of Stress Incontinence, British Journal of Obstetrics and Gynaecology, vol. 90, pp. 945-949 (Oct. 1983).

Klutke, Carl et al., The Anatomy of Stress Incontinence: Magentic Resonance Imaging of the Femal Bladder Neck and Urethra, The Journal of Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Klutke, John M.D. et al, The promise of tension-free vaginal tape for female SUI, Contemporary Urology, 7 pages (Oct. 2000).

Korda, A. et al., Experience With Silastic Slings for Female Urinary Incontinence, Aust NZ J. Obstet Gynaecol, vol. 29, pp. 150-154 (May 1989).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Kovac, Stephen Robert, M.D., Cirriculum Vitae, pp. 1-33 (Jun. 18, 1999).

Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1988).

Lichtenstein, Irving L. et al, The Tension Free Hernioplasty, The American Journal of Surgery, vol. 157 pp. 188-193 (Feb. 1989).

Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).

Luber; Karl M. et al., The Demographics of Pelvic Floor Disorders; Current Observations and Future Projections, Am J Obstet Gynecol, vol. 184, n. 7, pp. 1496-1503 (Jun. 2001).

Mage, Technique Chirurgicale, L'Interpostion D'Un Treillis Synthetique Dans La Cure Par Voie Vaginale Des Prolapsus Genitaux, J. Gynecol Obstet Biol Reprod, vol. 28, pp. 825-829 (1999).

Marchionni, Mauro et al., True Incidence of Vaginal Vault Prolapse—Thirteen Years of Experience, Journal of Reproductive Medicine, vol. 44, n. 8, pp. 679-684 (Aug. 199).

(56) References Cited

OTHER PUBLICATIONS

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Marshall, Victor Fray et al. The Correction of Stress Incontinence by Simple Vesicourethral Suspension, Surgery, Gynecology and Obstetrics, vol. 88, pp. 509-518 (1949).

Mcguire, Edward J. et al., Pubovaginal Sling Procedure for Stress Incontinence, The Journal of Urology, vol. 119, pp. 82-84 (Jan. 1978).

McGuire, Edward J. et al., Abdominal Procedures for Stress Incontinence, Urologic Clinics of North America, pp. 285-290, vol. 12, No. 2 (May 1985).

McGuire, Edward J. et al., Experience With Pubovaginal Slings for Urinary Incontinence at the University of Michigan, Journal of Urology, vol. 138, pp. 90-93(1987).

McGuire, Edwared J. et al., Abdominal Fascial Slings, Slings, Raz Female Urology, p. 369-375 (1996).

McGuire™ Suture Buide, The McGuire™ Suture Guide, a single use instrument designed for the placement of a suburethral sling, Bard, 2 pages (2001).

McIndoe, G. A. et al., The Aldridge Sling Procedure in the Treatment of Urinary Stress Incontinence, Aust. N Z Journal of Obstet Gynecology, pp. 238-239 (Aug. 1987).

McKiel, Charles F. Jr., et al, Marshall-Marchetti Procedure Modification, vol. 96, pp. 737-739 (Nov. 1966).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Morgan, J. E., A Sling Operation, Using Marlex Polypropylene Mesh, for the Treatment of Recurrent Stress Incontinence, Am. J. Obst. & Gynecol, pp. 369-377 (Feb. 1970).

Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Morley, George W. et al., Sacrospinous Ligament Fixations for Eversion of the Vagina, Am J Obstet Gyn, vol. 158, n. 4, pp. 872-881 (Apr. 1988).

Narik, G. et.al., A Simplified Sling Operation Suitable for Routine Use, Gynecological and Obstetrical Clinic, University of Vienna, vol. 84, No. 3, p. 400-405, (Aug. 1, 1962).

Natale, F. et al., Tension Free Cystocele Repair (TCR): Long-Term Follow-Up, International Urogynecology Journal, vol. 11, supp. 1, p. S51 (Oct. 2000).

Nichols, David H., The Mersilene Mesh Gauze-Hammock for Severe Urinary Stress Incontinence. Obstetrics and Gynecology, vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Norris, Jeffrey P, et al., Use of Synthetic Material in Sling Surgery: A Minimally Invasive Approach, Journal of Endourology, vol. 10, pp. 227-230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Ostergard, Donald R. et al., Urogynecology and Urodynamics Theory and Practice, pp. 569-579 (1996).

Paraiso et al., Laparoscopic Surgery for Enterocele, Vaginal Apex Prolapse and Rectocele, Int. Urogynecol J, vol. 10, pp. 223-229 (1999).

Parra, R. O., et al, Experience With a Simplified Technique for the Treatment of Female Stress Urinary Incontinence, British Journal of Urology, pp. 615-617 (1990).

Pelosi, Marco Antonio III et al., Pubic Bone Subuerthral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).

Peter E. Papa Petros et al., Cure of Stress Incontinence by Repair of External Anal Sphincter, Acta Obstet Gynecol Scand, vol. 69, Sup 153, p. 75 (1990).

Peter Petros et al., Anchoring the Midurethra Restores Bladder-Neck Anatomy and Continence, The Lancet, vol. 354, pp. 997-998 (Sep. 18, 1999).

Petros, Peter E. Papa et al., An Anatomical Basis for Success and Failure of Female Incontinence Surgery, Scandinavian Journal of Neurourology and Urodynamics, Sup 153. pp. 55-60 (1993).

Petros, Peter E. Papa et al , An Analysis of Rapid Pad Testing and the History for the Diagnosis of Stress Incontinence, Acta Obstet Gynecol Scand, vol. 71, pp. 529-536 (1992).

Petros, Peter E, Papa et al., An Integral Therrory of Female Urinary Incontinence, Acta Obstetricia et Gynecologica Scandinavica, vol. 69 Sup. 153, pp. 7-31 (1990).

Petros, Peter E. Papa et al., Bladder Instability in Women: A Premature Activation of the Micturition Reflex, Scandinavian Journal of Neurourology and Urodynamics, Sup 153, pp. 235-239 (1993).

Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).

Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).

Petros, Peter E. Papa et al., Further Development of the Intravaginal Slingplasty Procedure—IVS III —(With Midline "Tuck"), Scandinavian Journal of Neurourology and Urodynamics, Sup 153, pp. 69-71 (1993).

Petros, Peter E. Papa et al., Medium-Term Follow-Up of the Intravaginal Slingplasty Operation Indicates Minimal Deterioration of Urinary Continence With Time, (3 pages) (1999).

Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).

Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).

Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).

Petros, Peter E. Papa et al., Part III: Surgical Principles Deriving From the Theory, Scandinavian Journal of Neurourology and Urodynamics, Sup 153, pp. 41-52 (1993).

Petros, Peter E. Papa et al., Part IV: Surgical Appliations of the Theory—Development of the Intravaginal Sling Pklasty (IVS) Procedure, Scandinavian Journal of Neurourology and Urodynamics, Sub 153, pp. 53-54 (1993).

Petros, Peter E. Papa et al., Pinch Test for Diagnosis of Stress Urinary Incontinence, Acta Obstet Gynecol Scand, vol. 69, Sup 153, pp. 33-35 (1990).

Petros, Peter E. Papa et al., Pregnancy Effects on the Intravaginal Sling Operation Acta Obstet Gynecol Scand, vol. 69, Sup 153, pp. 77-79 (1990).

Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).

(56) References Cited

OTHER PUBLICATIONS

Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, pp. 73-75 (1993).
Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).
Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).
Petros, Peter E. Papa et al., The Role of a LAX Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II: Restoration of Dynamic Vaginal Supports by Infracoccygeal Sacropexy, an Axial Day-Case Vaginal Procedure, Int Urogynecol J, vol. 12, pp. 296-303 (2001).
Rackley, Raymond R. et al., Tension-Free Vaginal Tape and Percutaneous Vaginal Tape Sling Procedures, Techniques in Urology, vol. 7, No. 2, pp. 90-100 (2001).
Rackley, Raymond R. M.D., Synthetic Slings: Five Steps for Successful Placement, Urology Times, pp. 46,48,49 (Jun. 2000).
Raz, Shlomo, et al., The Raz Bladder Neck Suspension Results in 206 Patients, The Journal of Urology, pp. 845-846 (1992).
Raz, Shlomo, Female Urology, pp. 80-86, 369-398, 435-442 (1996).
Raz, Shlomo, MD, Modified Bladder Neck Suspension for Female Stress Incontinence, Urology, vol. XVII, No. 1, pp. 82-85 (Jan. 1981).
Richardson, David A. et al., Delayed Reaction to the Dacron Buttress Used in Urethropezy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clim obstet gynecol, vol. 25, pp. 897-912 (1982).
Ridley, John H., Appraisal of the Goebell-Grangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
Sabre™ Bioabsorbable Sling, Generation Now, Mentor, 4 pages (May 2002).
Sabre™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin, David R. et al., The Gore-Tex Sling Procedure for Female Sphincteric Incontinence: Indications, Technique, and Results, World Journal of Urology, vol. 15, pp. 295-299 (1997).
Studdiford, William E., Transplantation of Abdominal Fascia for the Relief or Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4; pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Swift, S.E., et al., Case-Control Study of Etiologic Factors in the Development of Sever Pelvic Organ Prolapse, Int Urogynecol J, vol. 12, pp. 187-192 (2001).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Sympton, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

(56) References Cited

OTHER PUBLICATIONS

Ulmsten, Ulf et al., Different Biochemical Composition of Connective Tissue in Continent, Acta Obstet Gynecol Scand, pp. 455-457 (1987).

Ulmsten, Ulf et al., Intravaginal Slingplasty (IVs): An Ambulatory Surgical Procedure for Treatment of Female Urinary Incontinence, Scand J Urol Nephrol, vol. 29, pp. 75-82 (1995).

Ulmsten, Ulf et al., The Unstable Female Urethra, Am. J. Obstet. Gynecol., vol. 144 No. 1, pp. 93-97 (Sep. 1, 1982).

Vesica® Percutaneous Bladder Neck Stabilization Kit, A New Approach to Bladder Neck Suspension, Microvasive ® Boston Scientific Corporation, 4 pages (1995).

Vesica® Sling Kits, Simplifying Sling Procedures, Microvasive® Boston Scientific Corporation, 4 pages (1998).

Villet, R., Reponse De R. Villet a L'Article De D. Dargent et al., Gynécolgie Obstétrique & Fertílité, vol. 31, p. 96 (2003).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Weber, Anne M. et al., Anterior Vaginal Prolapse: Review of Anatomy and Techniques of Surgical Repair, Obstetrics and Gynecology, vol. 89, n. 2, pp. 311-318 (Feb. 1, 1997).

Webster, George et al., Voiding Dysfunction Following Cystourethropexy: Its Evaluation and Management, The Journal of Urology, vol. 144, pp. 670-673 (Sep. 1990).

Winter, Chester C., Peripubic Urethropexy for Urinary Stress Incontinence in Women, Urology vol. XX, No. 4, pp. 408-411 (Oct. 1982).

Winters et al., Abdominal Sacral Colpopexy and Abdominal Enterocele Repair in the Management of Vaginal Vault Prolapse. Urology, vol. 56, supp. 6A, pp. 55-63 (2000).

Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert et al., Pulsion Enterocele: Long-Term Results of an Abdominoperineal Technique, Obstetrics & Gynecology, vol. 55 No. 2 pp. 141-148 (Feb. 1980).

Zacharin, Robert, The Suspensory Mechanism of the Female Urethra, Journal of Anatomy, vol. 97, Part 3, pp. 423-427 (1963).

Zimmern, Phillippe E. et al., Four-Corner Bladder Neck Suspension, Vaginal Surgery for the Urologist, vol. 2, No. 1, pp. 29-36 (Apr. 1994).

Mouly, Patnotc et al., Vaginal Reconstruction of a Complete Vaginal Prolapse: The Trans Obturator Repair, Journal of Urology, vol. 169, p. 183 (Apr. 2003).

Pourdeyhimi, B, Porosity of Surgical Mesh Fabrics: New Technology, J. Biomed. Mater. Res.: Applied Biomaterials, vol. 23, No. A1, pp. 145-152 (1989).

Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73.

Petros, Papa PE et al., An Integral Theory and Its Method for the Diagnosis and Management of Female Urinary Incontinence, Scandinavian Journal of Urology and Nephrology, Supplement 153: p. 1(1993).

Mentor Porges, Uratape, ICS/IUGA Symp, Jul. 2002.

\* cited by examiner

Fig. 2

METHODS AND IMPLANTS FOR TREATING URINARY INCONTINENCE

PRIORITY

The present non-provisional patent Application claims benefit from U.S. Provisional Patent Application having Ser. No. 61/085,247, filed on Jul. 31, 2008, by Knoll, and titled INSTRUMENT AND METHOD FOR PLACEMENT OF MALE INCONTINENCE REPAIR SLING, wherein the entirety of said provisional patent application is incorporated herein by reference.

FIELD OF THE INVENTION

The invention relates to treating incontinence in a male patient using a surgical sling secured internally to support a urethra, including methods, implants (e.g., slings), insertion tools, and related systems.

BACKGROUND

For patients with urinary incontinence, lives are perpetually interrupted by thoughts of ensuring that they have ready access to a restroom. Everyday activities such as attending a theater or sporting event can become unpleasant. Sufferers often begin to avoid social situations in an effort to reduce the stress associated with their condition.

A variety of treatment options are currently available for urinary incontinence. One type of surgical procedure found to be an especially successful treatment option for incontinence in both men and women, is a sling procedure. Sling procedures typically entail surgically implanting a biocompatible implant or "sling" to support the bladder neck or urethra. Sling procedures are discussed in U.S. Pat. Nos. 5,112,344; 5,611,515; 5,842,478; 5,860,425; 5,899,909; 6,039,686; 6,042,534; 6,110,101; 6,478,727; 6,638,211; and PCT Publication Nos. WO 02/39890 and WO 02/069781.

An implant for placement in a male patient may require greater strength, different (e.g., larger) dimensions, and better retention ability in tissue, relative to implants useful on a female patient. Also, methods of placement of such an implant can involve different tissue paths, incisions, and placement of implant features at alternate anatomy.

United States patent publication 2006/0287571 (U.S. Ser. No. 11/347,047) describes procedures to implant a urethral sling in a male anatomy. Described methods involve placement of a sling below a bulbous urethra, for example in contact with a corpus spongiosum. Steps of exemplified methods include creating a medial (e.g., perineal) incision, dissecting bulbospongiosus muscle to expose corpus spongiosum, and placing a central support portion of a sling in contact with the corpus spongiosum. Extension portions of the sling are extended through tissue paths to locations at which the extension portions can be secured to the patient, to thereby support the sling in place.

U.S. patent application Ser. No. 12/223,846, filed Aug. 8, 2008, by Ogdahl et al., titled SURGICAL ARTICLES AND METHODS FOR TREATING PELVIC CONDITIONS describes, inter alia, methods and devices for treating urinary incontinence in male patients. The methods involve a sling that includes two "soft tissue anchors" at opposite ends of a mesh strip. The sling is placed internally in a male patient through a medial incision, the sling supporting the urethra and the soft tissue anchors being placed internally, e.g., at opposing obturator foramen.

As with other established medical treatments, there is ongoing incentive and benefit in finding still improved treatments for urinary incontinence. Improvements may be in the form of new method steps, improved implants, improved insertion tools, and related systems and procedures.

SUMMARY

Methods as described are useful to treat urinary incontinence in a male by placing an implant to support the urethra. The implant includes a central support portion, extension portions extending from the central support portion, and soft tissue anchors. According to the method, the soft tissue anchors are placed at locations of soft tissue in a region of an obturator foramen. Placing a soft tissue anchor and a distal end of an extension portion at a region of an obturator foramen, preferably at tissue of endopelvic fascia, short of muscle tissue of the obturator foramen, i.e., on the bladder side of the obturator foramen, can allow placement of soft tissue anchors at locations away from nerves and blood vessels of the obturator foramen, and also away from the bladder.

Embodiments of the invention also relate at least in part to methods of treating urinary incontinence in a male patient by placing a sling (implant) to support a urethra, wherein the sling includes at least four soft tissue anchors located at ends of extension portions, two soft tissue anchors at distal ends of extension portions on opposing (e.g., left and right) sides of an implant.

Insertion tools can be used according to the methods, with implants as described. The insertion tools include a handle and elongate structure (e.g., one or multiple needles) extending from the handle to a location distal from the handle, that can engage one or two soft tissue anchors. E.g., the insertion tool can include two distal tip structures capable of engaging two soft tissue anchors on one side of an implant simultaneous, to allow handling and manipulation of the two soft tissue anchors and allow a user to place the two soft tissue anchors at soft tissue, together, in one step.

In one aspect the invention relates to an implant for treating urinary incontinence in a male. The implant includes: a central support portion comprising two opposing sides and two opposing ends, and capable of supporting a urethra; at least two extension portions extending from opposing sides of the central support portion, each extension portion comprising a proximal end attached to the central support portion, and a distal end; and four soft tissue anchors, each located at a distal end of an extension portion. When the central support portion is placed to support the urethra, the extension portions are capable of extending from the central support portion to soft tissue at a region of an obturator foramen.

In another aspect the invention relates to an insertion tool useful to place a sling for urinary incontinence. The insertion tool includes: a handle; a first needle comprising a proximal end and a distal end, the proximal end connected to the handle and the distal end adapted to engage a soft tissue anchor; and a second needle comprising a proximal end and a distal end, the proximal end connected to the handle and the distal end adapted to engage a soft tissue anchor.

In another aspect the invention relates to a method of treating urinary incontinence in a male. The method includes providing an implant comprising: a central support portion comprising two opposing sides and two opposing ends, and capable of supporting a urethra; at least two extension portions extending from opposing sides of the central support portion, each extension portion comprising a proximal end attached to the central support portion, and a distal end; and four soft tissue anchors, each located at a distal end of an extension portion, two on a right side of the implant and two on a left side of the implant. When the central support portion is placed to support the urethra, the extension portions are capable of extending from the central support portion to soft tissue at a region of an obturator foramen. The method further includes providing an insertion tool comprising: a first needle comprising a proximal end and a distal end, the proximal end connected to the handle and the distal end adapted to engage a soft tissue anchor; and a second needle comprising a proximal end and a distal end, the proximal end connected to the handle and the distal end adapted to engage a soft tissue anchor. The method further includes creating a medial incision at a perineum, placing the central support portion to support a urethra, engaging the two needle tips with two soft tissue anchors on a right side of the implant and placing the soft tissue anchors through tissue paths extending toward a region of an obturator foramen on one side of the patient, and engaging the two needle tips with two soft tissue anchors on a left side of the implant and placing the soft tissue anchors through tissue paths extending toward a region of an obturator foramen on another side of the patient.

The entireties of the content of all patent documents cited herein are incorporated herein by reference.

DETAILED DESCRIPTION

The following description is meant to be illustrative only and not limiting. Other embodiments of this invention will be apparent to those of ordinary skill in the art in view of this description.

The present invention is directed to surgical instruments, assemblies, and implantable articles for treating urinary incontinence in a male patient, e.g., stress urinary incontinence (SUI). Described are various features of surgical implants, surgical tools, surgical systems, surgical kits, and surgical methods, useful for installing implants. Useful implants can include a tissue support portion (or "central support portion") that can be used to support a urethra. Useful implants also include one or more extension portions (otherwise known as "end" portions or "arms") attached to the tissue support portion. Soft tissue anchors are attached at distal ends of extension portions, including at least two soft tissue anchors at distal ends of one or more extension portion on a first ("right") side of an implant and at least two soft tissue anchors at distal ends of one or more extension portion on a second ("left") side of an implant.

Methods as described are useful to treat incontinence in a male by placing an implant below a urethra, to support (i.e., support or approximate) the urethra. Soft tissue anchors are used to secure the implant at a desired supportive location, by securing the soft tissue anchors to internal soft tissue at regions of an obturator foramen. According to exemplary techniques, a physician (e.g., surgeon) is able place an implant at a location to support a male urethra, between locations at opposite obturator foramen, the implant being anchored internally by soft tissue anchors, the soft tissue anchors being placed at opposing regions of opposing obturator foramen. When the implant is placed, two soft tissue anchors, each located at a distal end of an extension portion, extend from the central support portion (below the urethra) to a region of an obturator foramen on one side of a patient, and two soft tissue anchors, each located at a distal end of an extension portion, extend to a region of an obturator foramen on an opposite side of a patient.

As used herein, tissue at a "region of an obturator foramen" refers to soft tissue within or proximal to an obturator foramen or surrounding pubic bone, specifically including endopelvic fascia, musculature (including musculature of the obturator foramen), and nearby ligaments, tendons, and muscle tissues. "Endopelvic fascia" refers to soft tissue between a bladder and a pelvic bone (i.e., musculature of the pelvic bone), including soft tissue that covers muscle attached to the pelvic floor and the obturator foramen, on the bladder side of the pelvic bone. Accordingly, endopelvic fascia includes tissue that is reached by creating a tissue path beginning at a location below a male urethra (e.g., below a bulbous urethra, optionally beginning at a corpus spongiosum or a bulbospongiosus muscle at a location below a bulbous urethra) and extending toward an obturator foramen to a location near but not in contact with (short of) the obturator internus muscle or nearby muscle tissues, as well as tissue that is proximate to such a tissue path.

An exemplary method of installing a male urethral sling can include a step of creating a perineal (e.g., medial) incision at the external male perineum; creating opposing tissue paths from the medial incision, below the urethra, to regions of the patient's left and right obturator foramen; and installing a urethral sling that includes extension portions with soft tissue anchors at distal ends, at regions of the opposing left and right obturator foramen. The implant includes at least two soft tissue anchors at distal ends of extension portions on each side of the implant, and the method includes placing at least two soft tissue anchors at a region of an obturator foramen on one side of the patient, and placing at least two soft tissue anchors at a region of an obturator foramen on a second (opposite) side of the patient.

Preferred methods of the invention can treat urinary incontinence in a male by supporting (meaning to support, position, re-position, or approximate) tissue of a urethra or a urethral sphincter complex, in any way that improves coaptation of the urethra, resulting in improved continence. According to one embodiment, a central support portion of a sling may be placed below the bulbospongiosus muscle and tensioned to re-position pelvic tissue and improve continence.

In preferred embodiments, a urethral sling can be installed in a male patient with the central support portion of the sling in direct contact with the corpus spongiosum. See U.S. Publication No. 2006-0287571. For example, a method can include providing a medial incision at the perineum of a male patient to a expose bulbospongiosus muscle, optionally and preferably dissecting through bulbospongiosus muscle to expose s corpus spongiosum, and placing a central support portion of a urethral sling in contact with the corpus spongiosum. Optionally the central support portion can be fixed to the corpus spongiosum, such as by use of a medical attachment in the form of a suture, staple, adhesive, or the like.

An insertion tool can engage soft tissue anchors on the implant, two soft tissue anchors on a right side of the implant and two soft tissue anchors on a left side of the implant. The insertion tool can be used to create a tissue path extending to a region of an obturator foramen, or to place the soft tissue anchors within a previously-prepared tissue path. The sling can be tensioned to approximate tissue at or around the urethra, to improve continence, and tension can optionally and preferably be maintained chronically.

In the exemplary embodiment, approximation of the corpus spongiosum can cause movement or relative movement of or between the urethra and the rhabdosphincter to allow the rhabdosphincter to better coapt the urethra and achieve improved or complete continence. Again not wishing to be bound by theory, approximating the corpus spongiosum may have the therapeutic effect of lifting and rotating tissue of the urethra, rhabdosphincter, or both, into a more physiologically normal position. As shown in FIG. 3, the urethra can be moved in a direction parallel to the length-wise direction of the urethra. Upon tissue ingrowth into the sling, the rhabdosphincter will have a more rigid backboard by which to operate against when collapsing the urethra. Improved positioning of the rhabdosphincter can be especially useful for men who have had the dorsal rhabdosphincter ruptured due to radical prostatectomy, and the muscle can no longer work against itself to collapse the urethra but rather needs to work against another rigid structure to be efficient.

Preferably, the soft tissue anchors include lateral extensions (e.g., two, of the same size and shape and form, extending in opposite directions from opposite sides of the base). The urethral sling may be placed using one or more insertion tools as described, by installing extension portions of the sling between the medial incision and regions of obturator foramen, with the central support portion of the sling positioned below the urethra. The extension portions may be pushed through the tissue path at the lead of an insertion tool that engages soft tissue anchors and pushes the soft tissue anchors through tissue. The tissue support portion (central portion) of the urethral sling may be placed as desired, below the male urethra, to support the urethra, optionally with approximation, compression, or a combination of approximation and compression. Adjustment of the implant can be performed based on the location (point of entry) and depth of insertion of soft tissue anchors within soft tissue of the opposing regions of obturator foramen. The central support portion may be placed below the bulbospongiosus muscle or below the corpus spongiosum, as desired. The sling may optionally include a widened central support portion that is placed to contact the corpus spongiosum, and the support portion and sling are used to approximate the urethra to improve continence, e.g., without the need for compression of the urethra. See, e.g., United States Publ. No. 2006/0287571 and U.S. Pat. No. 7,422,557.

Implant useful according to described methods can include a central support portion, extension portions extending from the central support portion, and soft tissue anchors at distal ends of the extension portions. In particular, implants can include at least four soft tissue anchors, each located at an end of an extension portions, e.g., two soft tissue anchors, each located at an end of one or more extension portion on, a right side of an implant; and two soft tissue anchors, each located at an end of one or more extension portion, on a left side of an implant.

The implant may include portions or sections that are synthetic or of biological material (e.g., porcine, cadaveric, etc.). Extension portions may be, e.g., a synthetic mesh such as a polypropylene mesh. The central support portion may be synthetic (e.g., a polypropylene mesh) or biologic. Examples of implant products that may be similar to those useful according to the present description, include those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, and Monarc® for treating urinary incontinence.

Exemplary implants can include a tissue support portion for placing in contact with tissue to be supported and one or more "extension" portions, the tissue support portion being useful to support a specific type of pelvic tissue such as the urethra, bladder, or vaginal tissue (anterior, posterior, apical, etc.). The tissue support portion can be sized and shaped to contact the desired tissue when installed, e.g., as a "sling" or "hammock," to contact and support pelvic tissue. A tissue support portion that is located between two or more extension or extension portions is sometimes referred to herein as a "central support portion" or a "support portion."

A central support portion is located between two (or more, e.g., four) opposing elongate extension portions. The central support portion may be integral with the extension portions as the same material, having the same (total) width and thickness, or may be of another material having different width and thickness dimensions. The central support portion is attachable to or integral with the extension portions and can be composed of a porous or non-porous plastic materials, a biologic material, or the like, such as a thermoplastic (e.g., polypropylene).

Extension portions are elongate pieces of material having a proximal end attached to the central support portion, and that extend away from the central support portion to a distal end. One or more soft tissue anchors can be connected to the distal end. The extension portion and soft tissue anchor (or anchors) can reach and be connected to a region of an obturator foramen to provide support for the central support portion. Two or more (e.g., four) extension portions can extend from the central support portion.

Examples of useful implants include supportive portions that include or consist of: a central support portion; either two or four elongate extension portions extending from the central support portion; and four soft tissue anchors, each soft tissue anchor at an end of an extension portion. The term "supportive portions" refers to portions of an implant that function to support tissue after the implant has been implanted, and specifically includes extension portions, central support portions, and soft tissue anchors, and does not include optional or appurtenant features of an implant such as a sheath, or a tensioning suture or other tensioning device. Examples of these implants include a central support portion and two extension portions, each extending from an opposite side of the central support portion and each having two soft tissue anchors located (side-by-side) at the ends of the extension portions. Other examples include a central support portion and four extension portions, two extension portions extending from each of opposite sides of the central support portion, and each of the four extension portions having a soft tissue anchor located at the distal end of the extension portion. With such implants, other optional feature may also be included, such as one or more tensioning sutures.

An implant may be integral, monolithic, or a composite of different components or segments of different synthetic or non-synthetic (e.g., "biologic") components. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Suitable synthetic materials for a sling include polymerics, metals, and plastics and any combination of such materials.

Examples of synthetic sling materials include polypropylene, cellulose, polyvinyl, silicone, polytetrafluoroethylene, polygalactin, Silastic, carbon-fiber, polyethylene, nylon, polyester (e.g. dacron) PLLA and PGA. The sling material may be resorbable, absorbable, or non-absorbable. Optionally, some portions may be absorbable and other portions may be non-absorbable. Commercial examples of synthetic materials useful in a urethral sling include Marlex™ (polypropylene) available from Bard of Covington, R.I., Prolene™ (polypropylene) and Mersilene (polyethylene terephthalate) Hernia Mesh available from Ethicon, of New Jersey, Gore-Tex™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon. Other examples of suitable materials include those disclosed in U.S. Pat. Publ. No. 2002/0072694.

Dimensions of an extension portion according to the invention can allow an extension portion to reach between a central support portion placed to support pelvic tissue (at an end of the extension portion connected to the tissue support portion) and a location at which the distal end of the extension portion attaches to pelvic tissue. A distal end of an extension portion, can include one or more soft tissue anchor tip that can be attached to tissue at a region of an obturator foramen, such as muscle, ligament, fascia, or other soft tissue. The length of the extension portion, therefore, can be in a range that allows placement of a tissue support portion as desired to support a urethra, while the soft tissue anchors are installed in tissue of a region of an obturator foramen.

The length of an implant ("length" refers to a dimension generally between opposing extension portions, including lengths of two opposing extension portions and a central support portion) between distal ends of extension portions, can be sufficient to place the central support portion below a urethra, to support the urethra, and to place opposing soft tissue anchors at opposing regions of a patient's obturator foramen. Exemplary lengths of an implant (L1 at FIG. 1) including lengths of two opposing extension portions and a central support portion (dimensions are measured while an implant lies flat), can be in the range from about 2 to 3 inches. Exemplary lengths of an extension portion (L2 at FIG. 1) can be in the range from about 0.8 to 1.2 inches (including a length of a soft tissue anchor). Exemplary lengths of a central support portion (L3 at FIG. 1) can be in the range from about 0.5 to 0.7 inches.

Placing a distal end of an extension portion at endopelvic fascia, short of muscle tissue of the obturator foramen, i.e., on the bladder side of the obturator foramen, can allow placement of soft tissue anchors at locations away from nerves and blood vessels of the obturator foramen, and also away from the bladder. Placing a distal end of an extension portion at endopelvic fascia, short of muscle tissue of the obturator foramen also allows for an extension portion of an implant to be slightly shorter than extension portions designed to anchor at obturator foramen musculature (e.g., obturator internus muscle or obturator externus muscle), or extension portions designed to pass through the obturator foramen (e.g., to an external incision).

Figure 1:
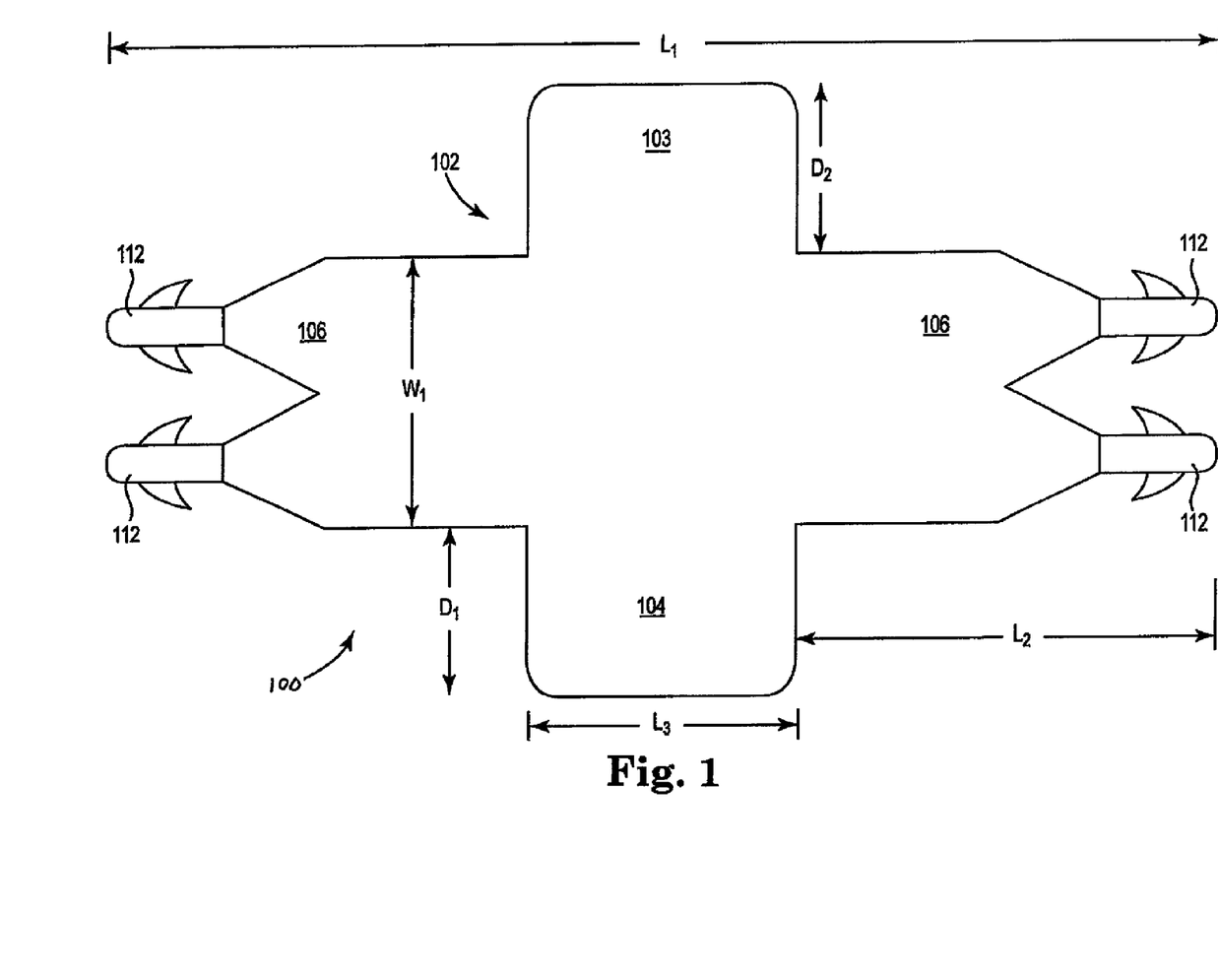
FIG. 1 shows an embodiment of an implant as described.
Figure 2:
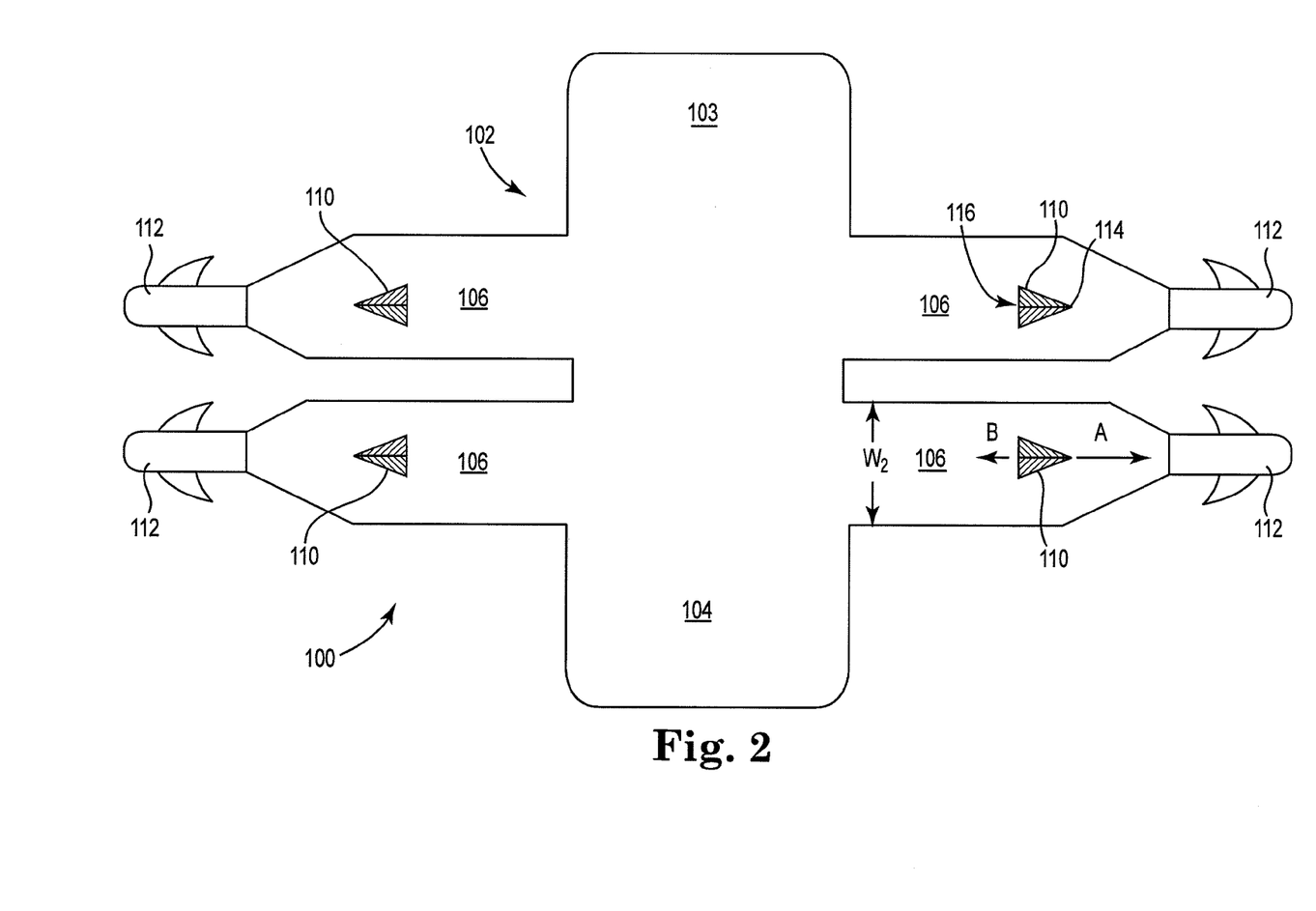
FIG. 2 shows an embodiment of an implant as described.

Not illustrated at FIGS. 1 and 2, but optionally a feature of an implant, opposing "bottom" (or posterior) extension portions can optionally be slightly shorter than the "top" (anterior) extension portions; when an implant is placed to support a urethra, a distance between a posterior location of the central support portion to a region of an obturator foramen may be less than a distance from an anterior location of the central support to a region of an obturator foramen. For example, a posterior extension portion may be from 0.2 to 0.4 inch shorter than an anterior extension portion.

Exemplary widths of an extension portion can be as desired, and may be based on factors including the number of extension portions extended from one side of a central support portion of an implant. FIG. 1 shows an implant having a total of two extension portions, one on each side of a central support portion, each extension portion having two soft tissue anchors at a distal end. A width (W1 at FIG. 1) of such extension portion, accommodating the presence of two soft tissue anchors, can be in the range from about 0.5 to 0.7 inches. Alternately, a width of an extension portion that accommodates only a single soft tissue anchors (see W2 at FIG. 2) can be approximately half of that width, such as from about 0.2 to 0.4 inches.

A preferred sling for placement against a corpus spongiosum may also include a central support portion that is wider than the one or more extension portions of an implant. A widened central support portion can provide improved mechanical and frictional engagement between the central support portion and the corpus spongiosum. A widened central support portion provides a larger area of contact between the sling and corpus spongiosum, and can have a reduced tendency to fold or deform upon tensioning of the sling. A suture can be used to attach the central support portion to the corpus spongiosum to further improve the area of contact and prevent folding, such as at a location on the anterior side of the central support portion. A suture may also be useful to prevent movement of the sling relative to the corpus spongiosum during or after installation or tensioning.

Exemplary widths of a central support portion can be as desired to support a male urethra as described herein, and may vary based on factors such as whether extended portions are desired, extending (forward and backward) beyond the total widths of the one or more extension portions on each side of a central support portion. FIG. 1 shows a central support portion that includes optional portions (lobes) extending forward and backward beyond the width of extension portions. The distance D1, which is the width of a lobe, can be as desired, e.g., from 0.3 to 0.5 inches. The width W1 of the median portion (the central support portion exclusive of lobes 103 and 104) of the central support portion matches the width W1 of the extension portions, and may be from about 0.5 to 0.7 inches. The distance D2, which is the width of the opposite lobe, can be as desired, e.g., from 0.3 to 0.5 inches.

An implant as described can include one or multiple soft tissue anchors located at distal ends of each extension portion. A soft tissue anchor can in general be a structure connected to a distal end of an extension portion, that can be implanted into soft tissue in a manner that will maintain the position of the soft tissue anchor and the attached implant. Preferred soft tissue anchors can also be designed to engage an end of an insertion tool (e.g., elongate needle, elongate tube, etc.) so the insertion tool can be used to push the soft tissue anchor through tissue or a pre-formed tissue path, for implantation. The soft tissue anchor may engage the insertion tool at an internal channel of the soft tissue anchor, at an external location such as at the base, or at a lateral extension, as desired. Examples of soft tissue anchors are described, e.g., in U.S. Ser. No. 12/223,846, filed Aug. 8, 2008, by Ogdahl et al., titled SURGICAL ARTICLES AND METHODS FOR TREATING PELVIC CONDITIONS.

A soft tissue anchor can be made of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

A soft tissue anchor can be located at a distal end of an extension portion, or along a length of an extension portion. Either type can have any general shape or design to allow an extension portion to be placed in and secured to soft tissue. Examples of useful soft tissue anchors can include one or more lateral extensions (e.g., teeth, barbs, hooks, tines, etc.) that can increase the force required to remove the soft tissue anchor from tissue after insertion into the tissue, i.e. the "pullout force." At the same time, an extension portion can be designed to exhibit a reduced or relatively low "insertion force," which is the amount of force used to insert the soft tissue anchor into tissue.

According to exemplary embodiments, a soft tissue anchor designed to attach to a distal end of an extension portion can have structure that includes a base having a proximal base end and a distal base end. The proximal base end can be connected (e.g., directly or indirectly) to a distal end of an extension portion. The base extends from the proximal base end to the distal base end and can optionally include an internal channel extending from the proximal base end at least partially along a length of the base toward the distal base end. An optional internal channel can be designed to interact with (i.e., engage) a distal end of an insertion tool to allow the insertion tool to be used to place the soft tissue anchor at a location within pelvic tissue of the patient.

Optionally, additional soft tissue anchors can be located at an extension portion, along a length of the extension portion at a location between a proximal end of an extension portion (attached to a central support portion) and a distal end of a support portion. These soft tissue anchors can extend from a surface or edge of an extension portion and can provide added support of the central support portion by increasing resistance to movement of the extension portion away from tissue of a region of obturator foramen. These soft tissue anchors may be in the form of a barb, hook, tooth, wedge, arrow, or otherwise-shaped structural feature that contacts soft tissue (fascia, e.g., endopelvic fascia) between a urethra and a location of a distal end of an installed extension portion, i.e., a location at a region of an obturator foramen. These soft tissue anchors can be made of materials as described herein, and can be constructed to adhere to or otherwise be attached to a surface or edge of an extension portion, with one or more extension portion being structured to contact and frictionally engage tissue.

Referring to FIG. 1, an exemplary embodiment of an implant is shown. Implant 100 includes central support portion 102, which includes a mid portion and two lobes, 103 and 104 (e.g., anterior and posterior lobes, collectively considered to be the central support portion). Two extension portions 106 extend from opposite sides (in dashed lines) of central support portion 102, from proximal ends connected to central support portion 102 to distal ends. At distal ends of each extension portion 106 are soft tissue anchors 112, which engage with implantation tools (not shown) and which can be placed in soft tissue. While not specifically illustrated, an implant as illustrated may include other appurtenant features such as edge extension reinforcement as described above (e.g., a reinforcing coating, reinforcing weave, reinforcing strand, heat treatment, etc.).

Referring to FIG. 2, implant 100 includes features similar to those of FIG. 1 and additionally includes two extensions portions 106 extending from each side of central support portion 102 (as opposed to the two extension portions illustrated at FIG. 1). The illustrated face of implant 100 of FIG. 2 also includes four additional soft tissue anchors 110 located on the illustrated side surfaces of extension portions 106 along lengths of extension portions 106 between proximal ends and distal ends. One such soft tissue anchor 110 is shown per extension portion 106, although more than one per extension portion can alternately be used. Also, the illustrated soft tissue anchors 110 are in the form of three-dimensional wedge-shaped soft tissue anchors having pointed distal end 114 and blunt proximal end 116. Other shapes that would allow for insertion of the extension portions in a (distal) direction toward a region of an obturator foramen (see arrow A) and result in resistance to motion in a opposite (proximal) direction (arrow B), will also be useful. As shown at FIG. 2, tissue anchors 110 are located on the illustrated side surfaces of implant 100; the other (non-illustrated) sides of each extension portion 106 can also, optionally, include one or more soft tissue anchors 110.

One or more insertion tool can be used to install an implant as described, by methods described. Various types of insertion tools are known that will be understood to be useful for placing an implant as described, having soft tissue anchors, to treat incontinence. These types of tools and modifications thereof can be used according to this description to install an implant. Examples of useful tools include those types of tools that generally include a thin elongate needle (optionally multiple needles, as described herein) attached to a handle; a handle attached to one end (a proximal end) of the needle; and a distal end of the needle adapted to engage a soft tissue anchor that allows the needle to push one or more soft tissue anchor through a tissue passage and insert the soft tissue anchor within tissue of the pelvic region. This class of tool can be used with a soft tissue anchor that includes an internal channel designed to engage a distal end of an insertion tool. Other general types of insertion tools will also be useful but may engage a soft tissue anchor in a manner that does not involve an internal channel of a soft tissue anchor. These alternate insertion tools may for example contact or grasp a proximal base end of a soft tissue anchor in the absence of an internal channel extending from the proximal base end toward the distal base end, such as by grasping an external surface of the base. An alternate insertion tool may contact or grasp a side of the base, a lateral extension, or any other portion of the soft tissue anchor or base, in a way that allows the insertion tool to hold the soft tissue anchor and insert the soft tissue anchor at a desired location within tissue of the pelvic region.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT application number 2006/028828; and PCT application number 2006/0260618; among others. Tools described in those patent documents are designed for placement of an implant in a pelvic region for the treatment of prolapse, male or female incontinence, etc. The tools of the above-referenced patent documents may be curved in two or three dimensions, and may include, for example, a two-dimensionally curved needle for placing an extension portion of an implant through a tissue path that passes from a region of the urethra to a region of an obturator foramen.

In certain embodiments, a tool can include a handle or a portion of a handle that exhibits a non-circular form when viewed along the longitudinal axis of the handle. The non-circular cross-section can be, e.g., an oval, rectangle, rhombus, etc., having one dimension "width" that is greater than the dimension perpendicular to that "width." The non-circular form will provide surfaces on the handle for a surgeon to place pressure onto and to achieve a grip. The non-circular crosssectional form can also preferably define a midplane that is a plane that includes the longitudinal axis of the handle and extends along the widest dimension of the handle when viewed in cross section.

Exemplary insertion tools can be similar to or can include features of tools described in the above-referenced patent documents. For use according to methods described herein, those insertion tools may be modified to allow the insertion tool to be used to accommodate implants as described, having two soft tissue anchors at ends of one or more extension portions, e.g., as illustrated at FIGS. 1 and 2. For example, an insertion tool can include two tips (or "engaging surfaces," e.g., distal ends of needles) or other structures that engage two soft tissue anchors simultaneously and (optionally) in a side-by-side configuration. The tips may conveniently be located at distal ends of two separate needles that extend side-by-side from a single handle. The tool can be designed to place two soft tissue anchors, side-by-side, at soft tissue at a region of an obturator foramen, e.g., two side-by-side needles can be sized and shaped to be inserted simultaneously through a medial incision (e.g., perineal incision in a male) and to extend from that incision to a location of an obturator foramen for placement of the two soft tissue anchors.

Exemplary insertion tools having two needles may include two needles that extend side-by-side in parallel or along identical curves from a proximal end connected to a handle to a distal end having a tip or other surface useful to engage a soft tissue anchor. According to these embodiments, two needles can optionally and preferably both connect to the handle at locations of a plane defined by a midplane of the handle. Exemplary sets of two curved needles can include the same curve (e.g., can be co-planar, parallel, or contained by a single curved plane). Each needle can include a distal end (tip) that engages a soft tissue anchor in a manner that allows the needle to push the soft tissue anchor through a tissue path and place the soft tissue anchor at a desired location of soft tissue at a region of an obturator foramen. Two engaging surfaces (tip) supported by a single handle allow the insertion tool to engage both soft tissue anchors simultaneously to push both soft tissue anchors into place in a single step.

Figures 3A, 3B, 3C:
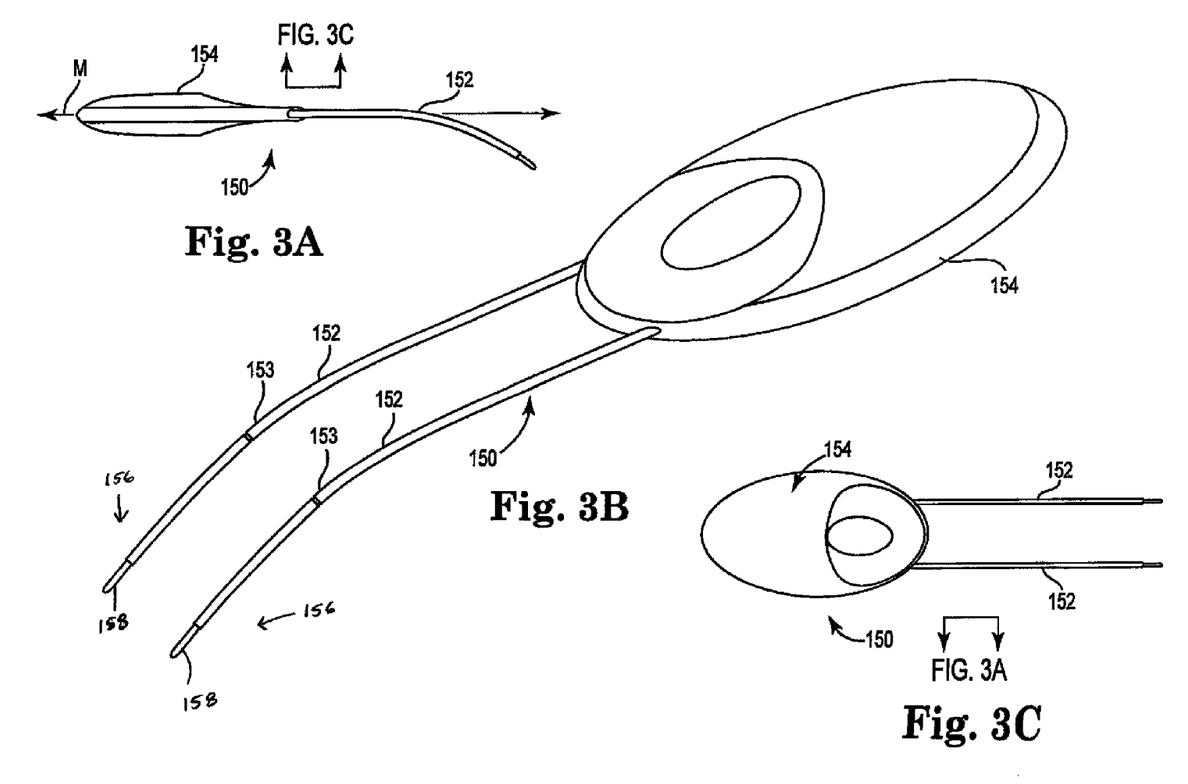
FIGS. 3A, 3B, and 3C shows an embodiment of an insertion tool as described.

An example of an embodiment of an insertion tool is shown at FIGS. 3A, 3B, and 3C. FIG. 3A is a side view, FIG. 3B is a front, top, perspective view, and FIG. 3C is a top view of insertion tool 150. As illustrated, insertion tool 150 includes two needles, 152, with proximal ends connected to an end of handle 154 and distal ends 156 including tips 158 for engaging soft tissue anchors (e.g., soft tissue anchors 112 of FIGS. 1 and 2). Handle 154 is of a non-circular shape to allow grasping and orientation; midplane (M at FIG. 3A) extends laterally through handle 154 and includes locations at which the proximal ends of needles 152 connect to handle 154. Markings 153 can be located to denote a desired length of insertion (of a needle) during a surgical procedure. The distance between needles 152 can be a distance that matches a distance between two soft tissue anchors located at one or more distal ends of one or more extension portion on one side of an implant, and may be, e.g., a distance in the range of 1.2 to 1.8 centimeters.

The invention also relates to surgical assemblies or kits for treating incontinence, including an implant and insertion tool as described and illustrated. An exemplary kit can include an implant as shown at FIG. 1 or 2 and an insertion tool as shown at FIG. 3A.

The invention claimed is:

1. A combination comprising an implant for treating urinary incontinence in a male, and an insertion tool, the implant comprising
    a central support portion comprising two opposing sides and two opposing ends, and capable of supporting a urethra,
    at least two extension portions, one extension portion extending from each of the two opposing sides of the central support portion, each extension portion comprising a proximal end attached to the central support portion, and a distal end, four soft tissue anchors, each located at one of the distal ends,
    wherein a first pair of soft tissue anchors is located on a first side of the central support portion and a second pair of soft tissue anchors is located on a second side of the central support portion, wherein when the central support portion is placed to support the urethra, the extension portions are capable of extending from the central support portion to soft tissue at a region of an obturator foramen, and
    the insertion tool comprising a handle, a first needle extending from the handle and comprising a first needle proximal end and a first needle distal end, the first needle proximal end in connected contact with the handle and the first needle distal end adapted to engage one of the soft tissue anchors at an end of an extension portion extending from the first side of the central support portion, and
    a second needle extending from the handle and comprising a second needle proximal end and a second needle distal end, the second needle proximal end in connected contact with the handle and the second needle distal end adapted to engage one of the soft tissue anchors at an end of an extension portion extending from the first side of the central support portion.

2. The combination according to claim 1 wherein the at least two extension portions comprise
    a left extension portion, and a right extension portion, and the first pair of soft tissue anchors is located at a distal end of the right extension portion and the second pair of soft tissue anchors is located at the distal end of the left extension portion.

3. The combination according to claim 1 wherein the extension portions have a width in the range from 2.4 to 4 centimeters and two soft tissue anchors of the first pair of soft tissue anchors are located at an end of one of the two extension portions and are approximately 1.2 to 1.6 centimeters apart in a side-by-side orientation.

4. The combination according to claim 1 wherein the at least two extension portions comprise a left anterior extension portion, a left posterior extension portion, a right anterior extension portion, and a right posterior extension portion, and one of said four soft tissue anchors at a distal end of each of the four extension portions.

5. The combination according to claim 4 wherein each posterior extension portion has a length that is shorter than each anterior extension portion.

6. The combination according to claim 4 wherein each extension portion has a width in the range from 1.2 to 1.8 centimeters.

7. The combination according to claim 1 wherein the tissue at a region of an obturator foramen is selected from endopelvic fascia, obturator internus muscle, and combinations thereof.

8. The combination according to claim 1 comprising at least one additional soft tissue anchor located along a length of one of the at least two extension portions between the proximal end and the distal end.

9. The combination according to claim 1 comprising at least two additional soft tissue anchors located along one of the at least two extension portions.

10. The combination according to claim 1 wherein the extension portions include a length in the range from 0.8 to 1.2 inches.

11. An insertion tool useful to place a sling for urinary incontinence, the insertion tool comprising a handle,
- a first needle in connected contact with the handle and comprising a first needle distal end adapted to engage a soft tissue anchor, and
- a second needle in connected contact with the handle and comprising a second needle distal end adapted to engage a soft tissue anchor, wherein a position of the first needle distal end is fixed relative to the handle and a position of the second needle distal end is fixed relative to the handle, the insertion tool, in combination with an implant, the implant comprising
- a central support portion comprising two opposing sides and two opposing ends, and capable of supporting a urethra,
- at least two extension portions extending from opposing sides of the central support portion, each extension portion comprising a proximal end attached to the central support portion, and a distal end,
- four soft tissue anchors, each located at a distal end of an extension portion,
- and adapted to engage the first or second needle,
- wherein when the central support portion is placed to support the urethra, the extension portions are capable of extending from the central support portion to soft tissue at a region of an obturator foramen.

12. The insertion tool according to claim 11 wherein a distance between a location on the handle of the first needle in connected contact with the handle and the first needle distal end, and a distance between a location on the handle of the second needle in connected contact with the handle and the second needle distal end, are the same.

13. The insertion tool according to claim 11 wherein the handle comprises a midplane and at least a portion of the first needle and at least a portion of the second needle lie in the midplane.

14. The insertion tool according to claim 11 wherein
the handle comprises a handle proximal end and a handle distal end,
the first needle comprises a first needle proximal end that extends from a first location at the handle distal end, and
the second needle comprises a second needle proximal end that extends from a second location at the handle distal end.

15. The insertion tool according to claim 14 wherein the first and second needles are of the same length, are straight or curved, and if curved exhibit the same curvature.

\* \* \* \* \*